US006509473B1

United States Patent
Drake

(10) Patent No.: US 6,509,473 B1
(45) Date of Patent: Jan. 21, 2003

(54) ENERGETIC TRIAZOLIUM SALTS

(75) Inventor: Greg W. Drake, Palmdale, CA (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 0 days.

(21) Appl. No.: 09/688,909

(22) Filed: Oct. 16, 2000

(51) Int. Cl.⁷ .................... C07D 249/08; C07D 249/14; C06B 25/34
(52) U.S. Cl. .................. 548/262.2; 149/92; 548/264.8; 548/265.2; 548/265.6
(58) Field of Search ............................ 548/262.2, 264.8, 548/265.2, 265.6; 149/92

(56) References Cited

U.S. PATENT DOCUMENTS

| | | | |
|---|---|---|---|
| 3,457,127 A | * 7/1969 | Cook et al. | 149/46 |
| 3,898,112 A | * 8/1975 | Strecker et al. | 149/19.9 |
| 5,099,028 A | * 3/1992 | Goe et al. | 548/265.6 |
| 5,198,204 A | 3/1993 | Bottaro et al. | |
| 5,254,324 A | * 10/1993 | Bottaro et al. | 423/263 |
| 5,256,792 A | * 10/1993 | Lee et al. | 548/263.8 |
| 5,274,105 A | * 12/1993 | Rothgery et al. | 548/263.8 |
| 5,472,647 A | * 12/1995 | Blau et al. | 264/3.1 |
| 5,684,269 A | 11/1997 | Barnes et al. | |
| 5,847,315 A | * 12/1998 | Katzakian, Jr. et al. | 149/19.9 |

FOREIGN PATENT DOCUMENTS

WO 20/60154 A1 * 10/2000

OTHER PUBLICATIONS

V.I. Sloveetskii et al, *Khim. Geter. Soedn.* 1966, 2, 448–452. (Russian authors).
G. Child, *J. Heterocycl. Chem.* 1965, 2, 98.

* cited by examiner

Primary Examiner—Robert W. Ramsuer
(74) Attorney, Agent, or Firm—Thomas C. Stover

(57) ABSTRACT

New energetic salts of 1,2,4-triazole; 3,4,5-triamino-1,2,4-triazole and of 4-amino 1,2,4-triazole were synthesized, characterized and their thermal and safety properties evaluated as possible new propellant ingredients. Energetic anions, including the nitrate anion, $NO_3$, the perchlorate anion, $ClO_4$, & the dinitramide anion, $N(NO_2)_2$, were paired with the protonated heterocycles through facile, high yield synthetic routes to give crystalline, energetic salts. Using such a heterocycle system, either 1,2,4-triazole; 3,4,5-triamino-1,2,4-triazole or 4-amino 1,2,4-triazole, a new family of salts were synthesized through the direct reaction of the heterocycle with the corresponding acid form of the desired anion. These reactions were carried out in commonly available polar solvents, and at ambient temperatures, to give high purity, high yield products. All of the salts which were synthesized, were put through thermal stability tests and through impact testing, to reveal a robust family of new insensitive materials, suitable as new energetic propellant ingredients.

9 Claims, No Drawings

ENERGETIC TRIAZOLIUM SALTS

STATEMENT OF GOVERNMENT INTEREST

The invention described herein may be manufactured and used by or for the Government for governmental purposes without the payment of any royalty thereon.

RELATED APPLICATIONS

NONE

FIELD OF THE INVENTION

This invention relates to methods of preparation of energetic salts, particularly of triazole (or triazolium) salts and the resulting salts.

BACKGROUND OF THE INVENTION

Presently, hydrazine is used in propellant scenarios, whether as a boost material or in altitude control devices. Hydrazine has several shortcomings, most which are inherent to the basic properties of the material. It has a relatively high vapor pressure at ambient temperature, 12–14 torr, which leads to vapor toxicological problems, and is also a known carcinogen. Its specific gravity is approximately 1.0 g/cm$^3$ at ambient temperatures. All of these properties can be significantly improved upon, with the use of new materials in monopropellant formulations.

In the prior art are U.S. Pat. Nos. 5,274,105 and 5,256,792, which disclose new energetic salts of high nitrogen heterocycles based on 1,2,4-triazole. But none are seen as pertinent to the claimed compositions.

Accordingly there is need and market for energetic propellant ingredients, which are easily synthesized in high yields, and have reduced vapor pressures at ambient temperatures and otherwise overcome the above prior art shortcomings.

There has now been discovered energetic salts which have reduced vapor pressures at ambient temperatures, significantly higher densities than hydrazine, improved specific impulse values and thermal stability. Also such salts can be made from commercially available starting materials in high yields, as discussed below.

SUMMARY OF THE INVENTION

Broadly, the present invention provides, an inventive method for preparing energetic, triazole (or triazolium) salts comprising, reacting the following:

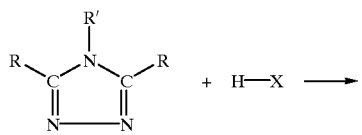

Substituted 1,2,4-triazole

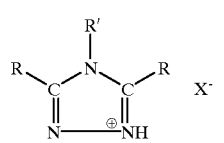

substituted 1,2,4-triazole salt where R and R' are H or NH$_2$, except that when R'=H, R=H; and X is NO$_3^-$, ClO$_4^-$, or N(NO$_2$)$_2^-$.

The invention also includes the above resulting salts and will become more apparent from the following detailed specificaton:

DESCRIPTION OF PREFERRED EMBODIMENTS

The energetic triazole salts of the invention are based on three heterocycle systems, 4-amino-1,2,4-triazole, 3,4,5-triamino-1,2,4-triazole, and 1,2,4-triazole. Two of the heterocycle systems are well known materials from the literature. 4-amino-1,2,4-triazole is readily synthesized from formic acid and hydrazine in the presence of certain catalysts. (U.S. Pat. No. 5,099,028; Org. Synth. 1944, 24, 12). While 3,4,5-triamino-1,2,4-triazole is easily synthesized in high yield and purity from the reaction of equivalent amounts of hydrazine with dimethylcyanamide under heating (J. Heterocyc. Chem. 1965, 2, 98). 1,2,4-triazole is commercially available. Once formed, these heterocycles can be reacted in a single reaction, in commonly available solvents, to form highly energetic salts of interest. The reaction is as follows.

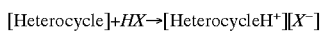

where HX=HNO$_3$, HClO$_4$ or HN(NO2)$_2$

In the above reaction, the heterocycle acts a proton acceptor from the strong acid HX. Once protonated, the heterocycle, [Heterocycle H$^+$], then pairs with the corresponding anion, X$^-$, to form a neutral salt which can be isolated as a pure material. The formed salts are stable materials with excellent thermal stability at elevated temperatures, and have desirable safety properties (impact and friction insensitivity).

1,2,4-triazole is commercially available. The other two triazole materials are readily available from one-step, high yield processes That is, 4-amino-1,2,4-triazole, which is a white crystalline, air-stable solid, with a melting point of 85° C., was synthesized readily from formic acid and hydrazine at elevated temperatures in the presence of an acid catalyst. (U.S. Pat. No. 5,099,028) (Reaction 1).

(1)

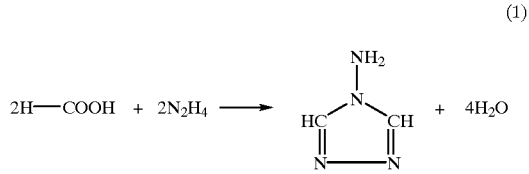

While 3,4,5-triamino-1,2,4-triazole, a white solid with a melting point of 254° C., was readily synthesized by heating equal amounts of dimethylcyanamide and hydrazine (J. Heterocyc. Chem. 1965, 2, 98) (Reaction 2).

(2)

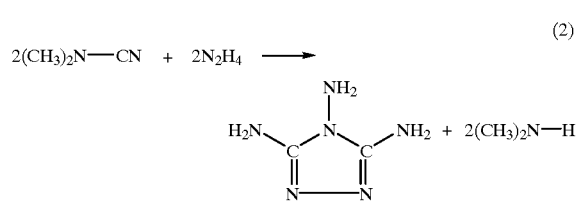

Energetic 4-amino-1,2,4-triazolium salts were synthesized in dry methanol, from reaction of the heterocycle with the desired form of the strong acid. All salts were formed in nearly quantitative yield and high purity (Reaction 3).

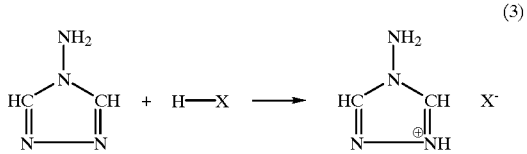

(3)

where H—X=HNO$_3$, HClO$_4$, or H—N(NO$_2$)$_2$.

For the synthesis of the nitrate and perchlorate salts, the concentrated, aqueous solutions of both acids, were used. For the synthesis of the dinitramide salt, since free dinitramine is known to be extremely explosive, the use of a strongly acidic, cation exchange resin bed was employed. Ammonium dinitramide, the starting material, was dissolved in anhydrous methanol, then eluted through the strong cation exchange resin, and into a methanol solution of 4-amino-1, 2,4-triazole.

All of the resultant salts of 4-amino-1,2,4-triazole have lower melting points than that of the starting heterocycle. The nitrate salt melted at 68° C., the perchlorate salt at 73° C., and the dinitramide salt melted at around 20° C. Both the nitrate and perchlorate salts of 4-amino-1,2,4-triazole were white crystalline solids. The dinitramide salt could not be made crystalline. However DSC studies of the dinitramide salt, revealed an endotherm indicative of a melt, at +20° C.

Synthetic endeavors with 3,4,5-triamino-1,2,4-triazole were similar to those involving the previous heterocycle, 4-amino-1,2,4-triazole (Reaction 4). The reaction was significantly slower, due to the poor solubility of the parent heterocycle in polar solvents.

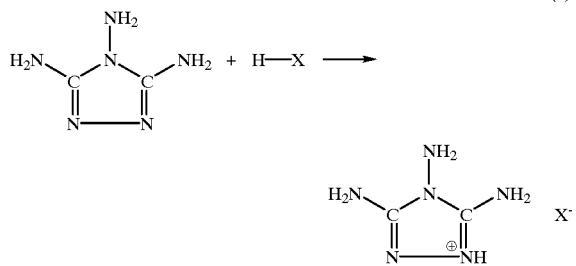

(4)

where H—X=HNO$_3$, HClO$_4$, or H—N(NO$_2$)$_2$

Upon completion of the reaction simple removal of the solvent by high vacuum, left highly crystalline, non-solvated salts. All of the product salts have relatively high melting points, the nitrate salt melted at 205° C., the perchlorate salt at 196° C., and the dinitramide salt melted at 145° C. The nitrate and dinitramide salts' melting points are impressive. Examples for comparison, include, guanidinium nitrate melt point of 214° C., while ammonium nitrate melts at 169° C. (*Explosives*, 4$^{th}$ *Edition*, VCH Germany, 1993). Ammonium dinitramide melts at 92° C., but doesn't decompose until 135° C. (U.S. Pat. No. 5,254,324).

The synthesis of the 1,2,4-triazole salts is identical to that of the 4-amino-1,2,4-triazole family (Reaction 5).

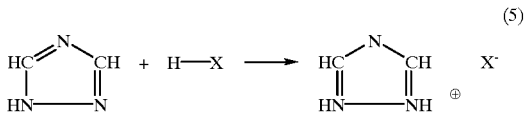

(5)

where H—X=HNO$_3$, HClO$_4$, or H—N(NO$_2$)$_2$.

The product 1,2,4-triazolium nitrate, was a white crystalline solid with a melting point of 137° C., while the perchlorate salt had much lower melting point of 89° C. The dinitramide salt was a white crystalline solid with a melting point of 75° C.

The following examples are intended to illustrate the invention and should not be construed in limitation thereof.

EXAMPLE 1

4-amino-1,2,4-triazole nitrate [C$_2$H$_5$N$_4$$^+$][NO$_3$$^-$]

Inside a nitrogen filled drybox, a Schlenk flask was charged with 0.9730 g, 11.6 mmoles, of 4-amino-1,2,4-triazole. Outside the drybox, the flask was attached to a double manifold, evacuated, and then charged with dry nitrogen. Dry, degassed, A.C.S. reagent grade methanol, 13 mL, was added through a disposable syringe along with a teflon stir bar under a brisk nitrogen flow. Concentrated nitric acid, A.C.S. reagent grade, 69–71%, 1.0702 g, 11.8 mmoles, was added with a disposable glass pipet under brisk nitrogen flow. The reaction mixture, which was a colorless, homogenous solution, was stirred for one hour at ambient temperature. At the end of one hour, the stir bar was removed, and the solvent was evacuated off with a high vacuum overnight. The next day, the white crystalline product, 4-amino-1,2,4-triazole nitrate remained in very high yield, 1.6416 g, 11.6 mmoles, or 96.4% of theory. M.P. 69° C. by DSC.

EXAMPLE 2

4-amino-1,2,4-triazole perchlorate [C$_2$H$_5$N$_4$$^+$] [ClO$_4$$^-$]

Inside a nitrogen filled drybox, a Schlenk flask was charged with 1.1469 g, 13.6 mmoles, of 4-amino-1,2,4-triazole. Outside the drybox, the flask was attached to a double manifold, evacuated, and then charged with dry nitrogen. Dry, degassed, A.C.S. reagent grade methanol, 13 mL, was added through a disposable syringe along with a teflon stir bar under a brisk nitrogen flow. Concentrated perchloric acid, A.C.S. reagent grade, 70%, 1.9966 g, 13.9 mmoles, was added with a disposable glass pipet under brisk nitrogen flow. The reaction mixture, which was a colorless, homogenous solution, was stirred for one hour at ambient temperature. At the end of one hour, the stir bar was removed, and the solvent was evacuated off with a high vacuum overnight. The next day, the white crystalline product, 4-amino-1,2,4-triazole perchlorate remained in very high yield, 2.4693 g, 13.4 mmoles, or 98.1% of theory. M.P. 73° C. by DSC.

EXAMPLE 3

4-amino-1,2,4-triazole dinitramide [C$_2$H$_5$N$_4$$^+$][N (NO$_2$)$_2$$^-$]

Inside a drybox, one Schlenk flask was charged with 1.8782 g, 22.3 mmoles of 4-amino-1,2,4-triazole, while another Schlenk flask was charged with 2.6453 g., 21.3 mmoles of ammonium dinitramide. Both flasks were removed from the drybox and attached to a double manifold, evacuated, and then charged with dry nitrogen gas. Subsequent manipulations of the reaction were carried out in total darkness, with only the assistance of a red light. Dry, degassed methanol was added to the ammonium dinitramide with a disposable syringe, which resulted in complete dissolution of the salt. The 4-amino-1,2,4-triazole was dissolved into 50 mL of dry methanol and transferred to a large round-bottomed flask, which was already attached to a medium fritted chromatography column. This column had been previously charged with a strong acidic cation exchange resin, which had been activated with 0. 1M HCl solution, followed by water elution to remove excess acid, followed by a solvent switchover to degassed, dry methanol. The ammonium dinitramide solution was then transferred to the top of the ion exchange column with a disposable syringe under vigorous nitrogen purge. The solution was then eluted through the column, with three aliquots, 50 mL each, of fresh of dry, degassed methanol, when solvent level was just above the ion exchange bed. At the end of the elution, the reaction flask was removed from the ion exchange column, and attached to a double manifold line, and the solvent removed over a 36 hour period, leaving a yellow oil in high yield, 4.0383 grams, 20.6 mmoles, 93% of theory. DSC revealed strong exotherm beginning around 150° C.

EXAMPLE 4

3,4,5-triamino-1,2,4-triazole nitrate, $[C_2H_7N_6^+][NO_3^-]$

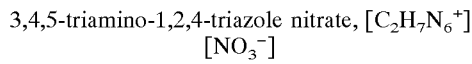

Inside a nitrogen filled drybox, a Schlenk flask was charged with 1.3848 g, 12.1 mmoles, of 3,4,5-triamino-1,2,4-triazole. Outside the drybox, the flask was attached to a double manifold, evacuated, and then charged with dry nitrogen. Degassed, deionized water, 12 mL, was added through a disposable syringe along with a teflon stir bar under a brisk nitrogen flow. Concentrated nitric acid, A.C.S. reagent grade, 69–71%, 1.1310 g, 12.2 mmoles, was added with a disposable glass, pipet under brisk nitrogen flow. The reaction mixture, which was a colorless, homogenous solution, was stirred for one hour at ambient temperature. At the end of one hour, the stir bar was removed, and the solvent was evacuated off with a high vacuum overnight. The next day, the white crystalline product, 3,4,5-triamino-1,2,4-triazole nitrate remained in very high yield, 2.1406 g, 12.1 mmoles, or 99.6% of theory. M.P. 206° C. by DSC.

EXAMPLE 5

3,4,5-triamino-1,2,4-triazole perchlorate, $[C_2H_7N_6^+][ClO_4^-]$

Inside a nitrogen filled drybox, a Schlenk flask was charged with 1.2758 g, 11.2 mmoles, of 3,4,5-triamino-1,2,4-triazole. Outside the drybox, the flask was attached to a double manifold, evacuated, and then charged with dry nitrogen. Degassed, deionized water, 12 mL, was added through a disposable syringe along with a teflon stir bar under a brisk nitrogen flow. Concentrated perchloric acid, A.C.S. reagent grade, 70.0%, 1.6073 g, 11.2 mmoles, was added with a disposable glass pipet under brisk nitrogen flow. The reaction mixture, which was a colorless, homogeous solution, was stirred for one hour at ambient temperature. At the end of one hour, the stir bar was removed, and the solvent was evacuated off with a high vacuum overnight. The next day, the white crystalline product, 3,4,5-triamino-1,2,4-triazole perchlorate remained in very high yield, 2.4180 g, 11.2 mmoles, or 100% of theory. M.P. 194° C. by DSC.

EXAMPLE 6

3,4,5-triamino-1,2,4-triazole dinitramide, $[C_2H_7N_6^+][N(NO_2)_2^-]$

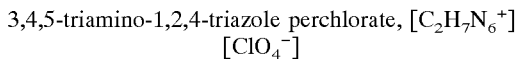

Inside a drybox, one Schlenk flask was charged with 1.3608 g, 11.9 mmoles of 3,4,5-triamino-1,2,4-triazole, while another Schlenk flask was charged with 1.5038 g., 12.1 mmoles of ammonium dinitramide. Both flasks were removed from the drybox and attached to a double manifold, evacuated, and then charged with dry nitrogen gas. Subsequent manipulations of the reaction were carried out in total darkness, with only the assistance of a red light. Dry, degassed methanol was added to the ammonium dinitramide with a disposable syringe, which resulted in complete dissolution of the salt. The 3,4,5-triamino-1,2,4-triazole was partially dissolved into 50 mL of dry methanol and transferred to a large round-bottomed flask, which was already attached to a medium fritted chromatography column. This column had been previously charged with a strong acidic cation exchange resin, which had been activated with 0. 1M HCl solution, followed by water elution to remove excess acid, followed by a solvent switchover to degassed, dry methanol. The ammonium dinitramide solution was then transferred to the top of the ion exchange column with a disposable syringe under vigorous nitrogen purge. The solution was then eluted through the column, with three aliquots, 50 mL each, of fresh of dry, degassed methanol, when the solvent level was just above the ion exchange bed. At the end of the elution, the reaction flask was removed from the ion exchange column, and attached to a double manifold line, and the solvent removed over a 36 hour period, leaving a yellow solid in high yield, 2.5140 grams, 11.4 mmoles, 95% of theory. M.P. 145° C. by DSC.

EXAMPLE 7

1,2,4-triazole nitrate $[C_2H_4N_3^+][NO_3^-]$

Inside a drybox, a flask was charged with 1.0458 g.; 15.1 mmoles, of 1,2,4 triazole. Outside the drybox, the flask was attached to a double manifold line and purged with nitrogen gas. Methanol, 20 ml, was added by a disposable syringe under vigorous nitrogen purge, along with a teflon stir bar, resulting in the complete dissolution of the heterocycle. Concentrated nitric acid, 1.3925 g, 15.2 mmoles, was added with a disposable pipet under vigorous nitrogen flow. Reaction mixture was allowed to stir for 30 minutes at ambient temperature, whereupon the stir bar was removed, and the solvent was evacuated off with a high vacuum overnight. After 18 hours of evacuation, a white crystalline solid remained in nearly quantitative yield, 1.9910 g, 99.6% of theory. Melting point 137° C. by DSC.

EXAMPLE 8

1,2,4-triazole perchlorate $[C_2H_4N_3^+][ClO_4^-]$

Inside a drybox, a flask was charged with 1.3745 g.; 19.9 mmoles, of 1,2,4 triazole. Outside the drybox, the flask was attached to a double manifold line and purged with nitrogen gas. Methanol, 15 ml was added by a disposable syringe under vigorous nitrogen purge, along with a teflon stir bar, resulting in the complete dissolution of the heterocycle. Concentrated perchloric acid, 2.8589 g, 19.9 mmoles, was added with a disposable pipet under vigorous nitrogen flow. After reaction was stirred for 30 minutes at ambient temperature, teflon stir bar was removed, and methanol was removed by evacuation overnight. Ethanol, 10 mL was added to the resultant solid, which, with warming, dissolved. 25 mL of diethylether was carefully layered on top of the ethanolic solution, and it was allowed to stand undisturbed. After 24 hours a large crop of crystals had formed. Crystals were washed with 3×10 mL of dry ether and vacuum dried, for a yield of 1.8579 g of product. The mother solution was layered with an additional 40 ml of diethyl ether yielding an additional 1.2863 g of product, for a total yield of 3.1442 grams, 93% of theory. Melting point: 89° C. (DSC)

EXAMPLE 9

1,2,4-triazole dinitramide $[C_2H_4N_3^+][N(NO_2)_2^-]$

Inside a drybox, one Schlenk flask was charged with 0.6801 g, 9.8 mmoles of 1,2,4-triazole, while another Schlenk flask was charged with 1.2103 g., 9.8 mmoles of ammonium dinitramide. Subsequent procedures were carried of in total darkness, in the presence of a red light only. Outside the drybox, dry methanol, 20 ml was added to both the 1,2,4-triazole and the $(NH_4)(N(NO_2)_2)$, dissolving both. The 1,2,4-triazole solution was transferred to a 1000 mL flask, with 3×20 ml aliquots of fresh methanol, and a large teflon stir bar was added. The ammonium dinitramide solution was added to the top of the ion exchange column with 3×10 ml of fresh methanol. The ammonium dinitramide solution was eluted at 2 drops/second into the vigorously stirred triazole solution. Three aliquots of fresh methanol (100 ml) were used to effect complete elution of the dinitramide solution. At the end of the elution, the methanol was rotovapped away, leaving a viscous, straw colored oil. The oil was transferred to a pre-weighed Schlenk flask, and further evacuated. The oil was then dissolved in 10 ml of dry ethyl acetate and layered carefully with 20 ml of dry, diethyl ether and stared at 4° C. for 48 hours. A large crop of crystals was recovered which was washed with fresh ether and was vacuum dried resulting in a yield of 1.6035 grams, 93% of theory. Melting point 75° C. by DSC.

In preparation of the above inventive salts, the reactants can be mixed in stoichiometric amounts (or with one or more reactants in excess) and at ambient temperatures and pressures or above or below same, within the scope of the invention.

The above highly energetic salts are new and inventive and can be used as indicated above. They can also be used in a gas generating system when mixed with an appropriate oxidizer or other highly energetic material.

These new salts have several advantages over the state of the art monopropellant-hydrazine, approximately a 50% increase in density, no vapor pressure at ambient temperature which results in lowered toxicity, higher predicted specific impulse values. The lowered toxicity will save considerable time and monies in the handling and loading of toxic materials such as hydrazine. These starting heterocycles are easily synthesized from commercially cheap starting materials in high yield processes. The subsequent reactions required in the formation are also very straightforward, facile, and high yield. The new salts involving 4-amino-1,2,4-triazole and 1,2,4-triazole are low melting solids or liquids, which hold promise in the field of liquid monopropellants. The new salts of 3,4,5-triamino-1,2,4-triazole are very high melting solids with high decomposition onset temperatures. Both families of salts have been found to be thermally stable at elevated temperatures for extended time periods, and both families of salts show low sensitivity values in standard impact and friction tests.

New energetic salts of 1,2,4-triazole; 3,4,5-triamino-1,2, 4-triazole and of 4-amino 1,2,4-triazole were synthesized, characterized and their thermal and safety properties evaluated as possible new propellant ingredients. Energetic anions, including the nitrate anion ($NO_3^-$) the perchlorate anion($ClO_4^-$) & the dinitramide anion ($N(NO_2)_2^-$), were paired with the protonated heterocycles through facile, high yield synthetic routes to give crystalline, energetic salts.

Using such heterocycle system, either 1,2,4-triazole; 3,4,5-triamino-1,2,4-triazole or 4-amino 1,2,4-triazole, a new family of (highly energetic, insensitive & crystalline) salts were synthesized through the direct reaction of the heterocycle with the corresponding acid form of the desired anion. These reactions were carried out in commonly available polar solvents, and at ambient temperatures, to give high purity, high yield products. All of the salts, which were synthesized, were put through thermal stability tests and through inpact and friction testing, to reveal a robust family of new insensitive materials, suitable as new energetic propellant ingredients.

Thus the energetic salts of the invention have negligible vapor pressure at ambient temperatures, significantly higher densities, (50–100%) than hydrazine, and breakthrough specific impulse values. A family of new energetic salts is described herein, which have facile synthetic routes from commercially available starting materials, high yields, excellent thermal stabilities, and desirable safety properties, including mechanical insensitivity.

These inventive salts can aid in producing higher performing propellants (liquid and solid) for increased payloads and/or cost savings. Commercial uses include reaction and attitude control propellants, booster propellants, gas generators and emergency power units. Companies employed in satellite development and production, vehicle restraint systems and space launch system development and production can benefit from the energetic salts of the present invention.

What is claimed is:

1. A method for making energetic triazole salts comprising, reacting the following:

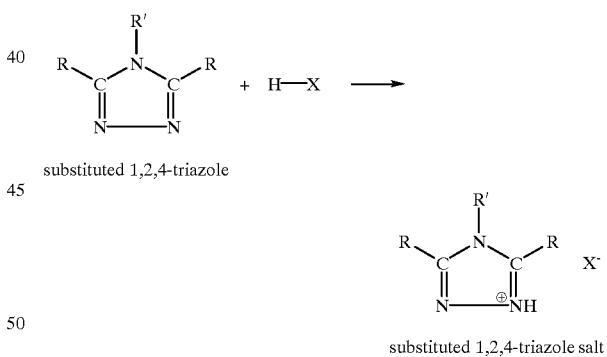

where R and R' are H or $NH_2$, except that when R'=H, R=H; and $X^-$ is $NO_3^-$; $ClO_4^-$; or $N(NO_2)_2^-$.

2. The method of claim 1 wherein:

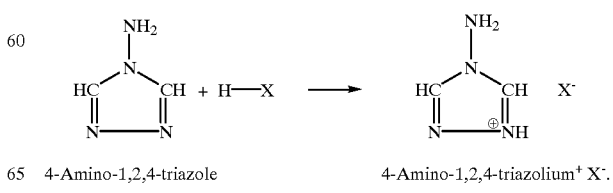

4-Amino-1,2,4-triazole      4-Amino-1,2,4-triazolium$^+$ $X^-$.

3. The method of claim 1 wherein:

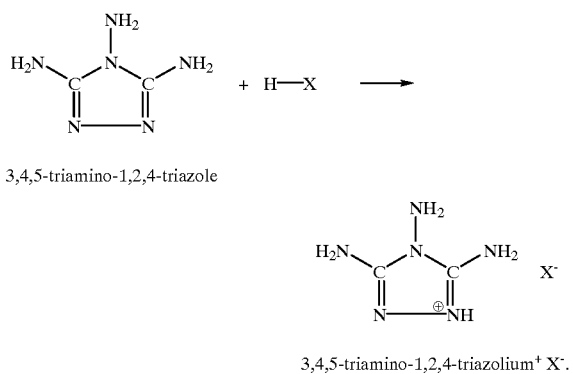

3,4,5-triamino-1,2,4-triazole 3,4,5-triamino-1,2,4-triazolium⁺ X⁻.

4. The method of claim 1 wherein:

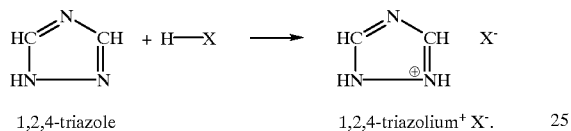

1,2,4-triazole           1,2,4-triazolium⁺ X⁻.

5. A triazole salt of the formula:

where R and R' are H or $NH_2$, except that when R'=H, R=H; and X⁻ is $NO_3^-$, $ClO_4^-$, or $N(NO_2)_2^-$.

6. A triazole salt of the formula:

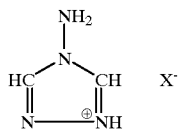

where X⁻ is as stated in claim 5.

7. A triazole salt of the formula:

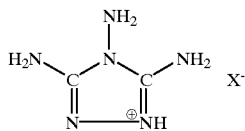

where X⁻ is as stated in claim 5.

8. A triazole salt of the formula:

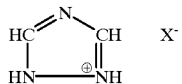

where X⁻ is as stated in claim 5.

9. A method of gas generating comprising employing the salt of claim 5 in a gas generating system.

* * * * *